United States Patent [19]

Bejtlich, III

[11] Patent Number: 5,581,017

[45] Date of Patent: Dec. 3, 1996

[54] INTEGRITY TEST FOR POROUS STRUCTURES USING ACOUSTIC EMISSION

[75] Inventor: Chester L. Bejtlich, III, Reading, Mass.

[73] Assignee: Millipore Investment Holdings Limited, Wilmington, Del.

[21] Appl. No.: 459,576

[22] Filed: Jun. 2, 1995

Related U.S. Application Data

[63] Continuation-in-part of Ser. No. 113,933, Aug. 30, 1993, abandoned.

[51] Int. Cl.$^6$ .................................................. G01N 21/85
[52] U.S. Cl. .......................... 73/38; 73/40.7; 73/24.02
[58] Field of Search ............................. 73/38, 40.5 A, 73/40.7, 24.02, 579; 356/430, 437; 250/343

[56] References Cited

U.S. PATENT DOCUMENTS

| | | | |
|---|---|---|---|
| 3,938,365 | 2/1976 | Dewey, Jr. | 73/24.02 |
| 4,622,845 | 11/1986 | Ryan et al. | 73/24.02 |
| 4,817,413 | 4/1989 | Asano et al. | 73/24.02 |
| 5,161,408 | 11/1992 | McRae et al. | 73/40.7 |

OTHER PUBLICATIONS

Knight et al. "New Integrity Test Method", 8th Annual Membrane Planning Conferece, pp. 1–10 Oct. 1990.

*Primary Examiner*—Michael Brock
*Attorney, Agent, or Firm*—Andrew T. Karnakis

[57] ABSTRACT

A rapid, highly sensitive determination, in-situ, of the integrity and/or pore size distribution of a porous membrane structure (e.g. a pleated membrane filter cartridge) is disclosed. The identification of the integrity and/or pore size characteristics involves interpreting the residence time distribution (RTD) of the membrane structure under test and includes using a tracer gas in mixture with a carrier gas as part of a diffusion or bubble-point test. The tracer gas mixture exiting the downstream surface of the membrane becomes moisturized and is excited with a pulsed (or otherwise modulated) light source at a wavelength corresponding to the absorption line of the tracer gas. The frequency of modulation is chosen such that the tracer gas preferentially generates a photo-acoustic emission while the emission due to the absorption of water present is suppressed. The detected pressure pulse is processed to produce electrical signals indicative of the concentration of tracer gas that passes through the membrane. A non-integral (or incorrect pore size) device will demonstrate a characteristic RTD that differs from an integral (or correct pore size) device in either/or (or both) the onset time prior to tracer gas detection and the rate of change of tracer gas concentration with time.

22 Claims, 6 Drawing Sheets

INTEGRITY TEST FOR POROUS STRUCTURES USING ACOUSTIC EMISSION

This is a continuation-in-part of application Ser. No. 08/113,933 filed on Aug. 30, 1993, now abandoned.

BACKGROUND OF THE INVENTION

This invention relates generally to a method and apparatus for determining both the pore-size characteristics and integrity of porous structures, particularly membrane filters and fabricated devices incorporating such filters. Specifically, this invention relates to a method and apparatus for determining the pore-size characteristics and/or integrity of a membrane filter based upon diffusion testing involving the use of test measurement gases and photo-acoustic generation/detection techniques.

Presently, the pore-size characterization and determination of integrity for membranes and filters, in general, are performed using procedures which are referred to as, among other things, "air-flow porosimetry", the "bubble-point test" or "bubble-point determination", and the "diffusion test". In addition, hydrophobic membranes, specifically, can also be characterized and tested by procedures referred to as, among other things, the "water intrusion-pressure determination" and the "water flow test" or "water intrusion test". U.S. patent application Ser. No. 08/105,525, now U.S. Pat. No. 5,477,155, assigned to the same assignee as the present application, describes a variation of the water intrusion method in which electrically conductive liquids are used to identify the pressure at which the liquid intrudes into and through the pores of the membrane, The bubble-point test and air-flow porosimetry utilize a liquid which spontaneously wets the membrane in question to create a barrier to gas flow. Subsequent attempts to displace the wetting liquid with a gas require that the gas pressure be elevated to some critical level dependent on the size of the pores, or the size of defects, if present, in order to overcome the surface-tension forces holding the liquid in the pores. The equation for this critical pressure, defined as the bubble-point pressure, is a variation of the Young-Laplace equation for capillary pressure drop, in this application often called the Washburn equation:

$$P_{BUBBLE\ POINT} = 4 K \sigma \cos(\theta)/d \quad \text{(Equation 1)}$$

where;

$P_{BUBBLE\ POINT}$ = bubble-point pressure

K = the pore perimeter (shape) correction factor $\sigma$ = surface tension of the liquid $\theta$ = contact angle of the liquid against the solid d = the diameter of the pore Equation 1 is rarely actually used to quantitatively calculate a pore size from empirical bubble-point data, since the pore perimeter correction factor, K, is rarely known independently. Instead, since this equation indicates that the bubble point is inversely related to the pore diameter, it is used to qualitatively rank the relative pore size of membranes according to their bubble-point pressures. Further, since particle retention efficiency is related to the pore size, Equation 1 is also used to justify an empirical correlation between the retention efficiency of membranes of various pore sizes to their bubble points. Membrane manufacturers and users have taken advantage of this retention vs. bubble point relationship to identify the critical bubble point required for a desired level of retention, and membrane filter users conduct bubble point determinations to confirm that the filter in question is integral and of the appropriate pore size. Integral refers to the fact that the filter element will have the desired level of retention and contains no defects or large pores that diminish this desired level of retention.

Air-flow porosimetry and a visual version of the bubble-point test for membrane samples are described by ASTM Method F316-86. In general, the bubble-point test is performed by pre-wetting the membrane with an appropriate liquid and mounting the membrane in a specially designed holder which allows a visually observable layer of liquid to be placed on the downstream, i.e., in this configuration, upper side of the membrane. In the case of a bubble-point test of an enclosed filter, the filter is flushed with the liquid to wet the membrane. The pressure of air or other gas on the upstream side of the membrane is then increased, and the downstream liquid layer or the outlet from the enclosed filter is observed for the formation of continuous streams of bubbles. The pressure at which these bubbles first appear is called the bubble-point pressure of the membrane.

For relatively large membrane filters, which as discussed below experience significant rates of gas diffusion at pressures below the bubble point, a more analytical method is used to determine the bubble-point pressure. In this case, the rate of flow of gas through the filter is measured as a function of the imposed gas pressure, and the pressure at which the flow makes a transition from relatively low flow rates, which are indicative of diffusion only, to significantly higher flow rates, which are indicative of bulk gas flow through pores or defects, is referred to as the bubble-point pressure of the filter. This method has been described in a presentation by Knight and Badenhop at the 8th Annual Membrane Planning Conference, held Oct. 15–17, 1990.

Porosimetry is used to determine the relative pore-size distribution of a membrane or membrane filter. In this procedure, the flow rate of gas through a pre-wetted membrane at a particular gas pressure is divided by the flow rate of gas through an initially dry identical membrane at the same pressure. The resulting mathematical ratio, R, is plotted as a function of imposed pressure, and the first derivative of this function, dR/dP, yields a bubble-point pressure distribution, which, via the bubble-point equation (Equation 1), also indicates the relative distribution of pore sizes.

The diffusion test is used primarily for relatively large filter areas and indicates whether or not the filter is integral by measuring the gas flow rate of a test gas through the filter when exposed to a constant upstream gas pressure equal to, or slightly below, the minimum bubble-point pressure required for the filter. Similar to a bubble-point test, the filter is pre-wet with an appropriate liquid. At a properly selected test pressure, the measured flow rate of the test gas will be relatively low (indicative of diffusive as opposed to convective flow) when the filter is integral and of the pore size appropriate for the selected test pressure. The source of gas flow through an integral filter at pressures below the actual bubble point of the filter can be attributed to dissolution of gas into, diffusion through, and re-evaporation from the liquid filling the pores, without forcing the liquid out of the pores. In such a test, a filter with an undesirable large pore size or with a defect will exhibit relatively large gas flow rates of the test gas as a result of the test pressure being in excess of the bubble-point pressure attributed to the defect.

In practice, both diffusion and bubble-point test measurements are conducted in two ways, namely a direct measurement of mass flow of the gas or an indirect pressure decay measurement. In the mass flow measurement, the flow rate of the transport gas is measured directly after steady state is achieved. A pressure decay measurement is performed by isolating the volume upstream of the membrane after achieving the desired test pressure and monitoring decay of pressure as the gas occupying this volume is depleted by either diffusional or convective transport through the wetted membrane. A single measurement is generally made after 2 to 5 minutes. The sensitivity of both techniques is limited by the solubility of the gas in the wetting medium since this solubility controls the background diffusion or noise level. In a defective element, the increased gas flow associated with defects must be quantifiably above this background diffusion level.

A more sensitive test can be designed based upon the principles of dynamic residence time distribution (RTD) measurements. This is a standard technique used to determine the hydrodynamic and fluid mixing properties of vessels. As applied to membrane filter integrity testing, a diffusion test would be performed in the conventional manner. However, a second detector gas would be used to perform the measurement. In its simplest form, the upstream surface of the liquid-filled membrane is contacted with a gas, such as air, which is used in this case as a carrier gas. A second tracer gas, such as sulfur hexafluoride, either premixed with the carrier gas or alone, is injected into the air-carrier gas upstream of the membrane surface and elevated to the desired trans-membrane test pressure. The sulfur hexafluoride is added permanently to the carrier gas such that the total trans-membrane pressure remains constant. Alternatively, the tracer gas can be injected as a pulse into the carrier gas which is elevated to the test trans-membrane pressure. The concentration of the tracer gas is then monitored as a function of time on the downstream side of the membrane. The transport of the tracer gas across an integral membrane unit is controlled by diffusion as described above. However, in a non-integral membrane unit, the test pressure will exceed the bubble point of large defects, the pores are evacuated of liquid and the transport of the tracer gas is governed by convective or bulk flow. Since bulk flow will transport gas much faster than diffusion, use of the RTD measurement technique results in a significant sensitivity benefit over the quasi-steady state diffusional measurement conventionally practiced. It should be noted that this process can be conducted at non-constant trans-membrane pressure.

The RTD technique was first described as a method for integrity testing a cartridge membrane filter in the aforementioned presentation by Knight and Badenhop. In this presentation, a method is described in which a water-wetted membrane unit is challenged at a trans-membrane pressure near the characteristic bubble point of the membrane with air, the carrier gas. After steady state is achieved, the detector gas, sulfur hexafluoride, is introduced into the incoming air stream while maintaining a constant applied pressure. The concentration of the sulfur hexafluoride is monitored in the volume downstream of the membrane cartridge. This method demonstrated sensitivity that greatly exceeded conventional diffusion techniques. However, the method described by Knight and Badenhop is severely limited by the analytical procedures employed. Grab-samples of the downstream gas are collected using an elaborate sample collection assembly intended to avoid sample contamination. The sulfur hexafluoride concentration is then measured off-line using an electron capture device that includes a gas chromatograph pre-treatment to remove moisture from the sample. The relatively long analysis time and re-equilibration time between individual batch samples conducted off-line inhibit this approach from having practical value as a routine test for determining integrity or pore size distribution.

Photo-acoustic spectroscopy is a well established technique for detecting trace quantities of gas (see Kreuzer 1971, J. Appl. Phys. 42 p2934–2943; Kreuzer and Patel 1971, Science 173, p45–47). In this conventional technique, a gas sample is irradiated by a chopped laser beam. When the laser wavelength coincides with an absorption line of the gas to be detected, the absorption of the radiation produces temperature and pressure increases in the gas. The subsequent re-emission results in pressure oscillations that are detected with a microphone. In the conventional technique both the sample gas and the microphone detector are co-located within a closed cell. This photo-acoustic technique has been extended by remoting the microphone detector away from the sample chamber as described by Brassington 1982, J. Phys. D. Appl. Phys. 15, p219–228, thus enabling remote leak detection.

Several device configurations are described in the prior art for conducting photo acoustic detection. For example, U.S. Pat. No. 4,557,603 to Oehler et al. discloses the use of a monochromator to vary the wavelength of the light, and U.S. Pat. No. 4,622,845 to Ryan et al. discloses the use of a pulsed infrared light source and an acousto-optical tunable filter to provide the desired wavelength of light.

U.S. Pat. No. 5,161,408 to McRae et al. discloses an apparatus that uses a monochromatic laser of known fixed wavelength which is strongly absorbed only by sulfur hexafluoride ($SF_6$) gas. The laser beam employed by McRae et al. scans a two dimensional field in the test area of a container or other gas or liquid-tight component. Any trace $SF_6$ gas excited by the scanned laser beam will produce an audible sound that is detected by a microphone. A discriminating electronic circuit is disclosed to process the electronic signal from the microphone. The prior art with respect to photo-acoustic detection has typically addressed various devices for applying external photo-acoustic techniques to the determination of leak detection from systems intended to be gas-tight or liquid-tight. In these systems the measurement conditions are binary in nature, that is the system is only concerned with distinguishing between a normal condition where there is zero flow of tracer gas and an abnormal condition where some discernible flow is detected. The concentration level of the gases being detected is of minimal importance in such systems. Oehler et al. in U.S. Pat. No. 4,740,086 makes reference to measuring the permeability of gas-permeable elements using photo-acoustic detection with their apparatus; however, bulk gas permeability measurement is altogether different from measuring the pore size or determining the integrity of a porous membrane element which requires discriminating between holes (pores) of different sizes. Moreover, no mention is made in the prior art of making photo-acoustic detection measurements in a moisturized gas. Thus in these systems the background signal, assuming that the laser is specifically tuned only to the tracer gas, is negligible. Consequently, in these systems the interpretation of the signal produced by the photo-acoustic effect is greatly simplified.

SUMMARY OF THE INVENTION

The foregoing limitations and disadvantages of the prior art are overcome by the present invention which incorporates a photo-acoustic detection system as applied to the rapid, sensitive determination, in-situ, of the integrity and/or pore size distribution of a porous membrane structure. The membrane structure is water-wetted to create a barrier to convective gas flow and then challenged with a mixture of a carrier and a tracer gas at a trans-membrane pressure equal to, or near, the acceptable bubble point (or other characteristic pressure) of the structure. The carrier and tracer gas mixture exits the downstream surface of the membrane as a moisturized (i.e. water or water vapor containing) gas mixture. A photo-acoustic detection system monitors the tracer gas concentration on the downstream side of the membrane structure as a function of time. Both an integral membrane unit as well as a non-integral unit will produce a measurable signal. The dynamic signal produced from each type of unit has two characteristics that can be compared to determine the integrity of the membrane structure. These are the onset (or lag) time until a signal indicative of gas concentration passes a threshold value and thus appears on the downstream side of the membrane structure; and/or the rate of change of the tracer gas concentration on the downstream side. Similarly, the signal integrated over time can be used as a measure of the total mass of tracer gas transported.

The invention presented in this application provides a sensitive and rapid method for the identification of the integrity and/or pore size characteristics of a membrane or other porous material and/or fabricated membrane device in-situ and in real time by measuring the concentration of tracer gas in the presence of an interfering background signal (e.g. water). This method is based upon the interpretation of the residence time distribution characteristics of the membrane device. The preferred method of this invention comprises testing a membrane that is wet with a liquid using a tracer gas, which is soluable in the liquid, in mixture with a carrier gas as a challenge gas in a conventional diffusion or bubble-point test, exciting the moisturized tracer gas mixture downstream of the membrane (or for fabricated devices, within the cartridge core or outlet porting) with a pulsed or otherwise modulated monochromatic light source at a fixed wavelength that coincides with the absorption line of the tracer gas to produce a photo-acoustic effect, and detecting the resultant acoustic wave by a remote pressure transducer, such as a microphone, located on the downstream side of the filter. In order to discriminate between the component of interest (e.g. tracer gas) and the additional, undesired artifact present in the mixture (e.g. water or water vapor), which also absorbs light energy at the same wavelength, the light source is modulated at a frequency which preferentially generates an acoustic emission corresponding to the component of interest while suppressing the emission corresponding to the interfering component. The desired frequency modulation may be accomplished by scanning all or a portion of the volume downstream of the membrane or by chopping the incident light beam. The RTD of an integral membrane and/or device will exhibit a characteristic non-linear rise in tracer gas concentration asymptotically reaching a steady-state value corresponding to diffusional flow of tracer gas through the liquid-filled membrane. This concentration rise is monitored in time through the photo-acoustic effect created by illuminating the downstream volume of the filter with the rastored, or otherwise modulated, laser. A non-integral device will demonstrate a characteristic RTD that will differ from that of an integral device in either/or (or both) the onset time prior to tracer gas detection and the rate of change of tracer gas concentration with time.

The preferred apparatus used in this invention comprises a membrane filter product (e.g. cartridge filter) within a closed housing such that the upstream surface is sealed and isolated from the downstream surface. A tracer gas, or a mixture of tracer and carrier gas, is introduced either uniformly or non-uniformly to the upstream surface of a water-wet membrane at an elevated applied pressure. A pulsed or otherwise modulated monochromatic light source is directed into the volume downstream from the membrane. Moisturized tracer gas exiting the liquid-filled membrane enters the downstream volume and a signal corresponding to the concentration of tracer gas per se will be detected when excited by the modulated light source. The pressure transducer, e.g. a microphone, is located in the volume downstream of the filter, such as within a connecting tube external to the housing of the cartridge filter or within the cartridge central core, which is illuminated by the light source.

The tracer gas can be one of several, including sulfur hexafluoride, carbon dioxide and water vapor, that have a corresponding easily attainable absorption line corresponding to the wavelength of a monochromatic light source. Of these, the combination of sulfur hexafluoride gas and a carbon dioxide laser provide a very sensitive, easily attainable combination that is non-destructive and non-contaminating to the membrane filter element. Moreover, this combination is inexpensive to execute on a commercial scale.

In other embodiments, the microphone may be located in other locations on the downstream side of the filter, such as inside the central core of a pleated cartridge. Similarly, both lasers and flash lamps can be used as the light source.

DESCRIPTION OF THE PREFERRED EMBODIMENT

Figure 1:
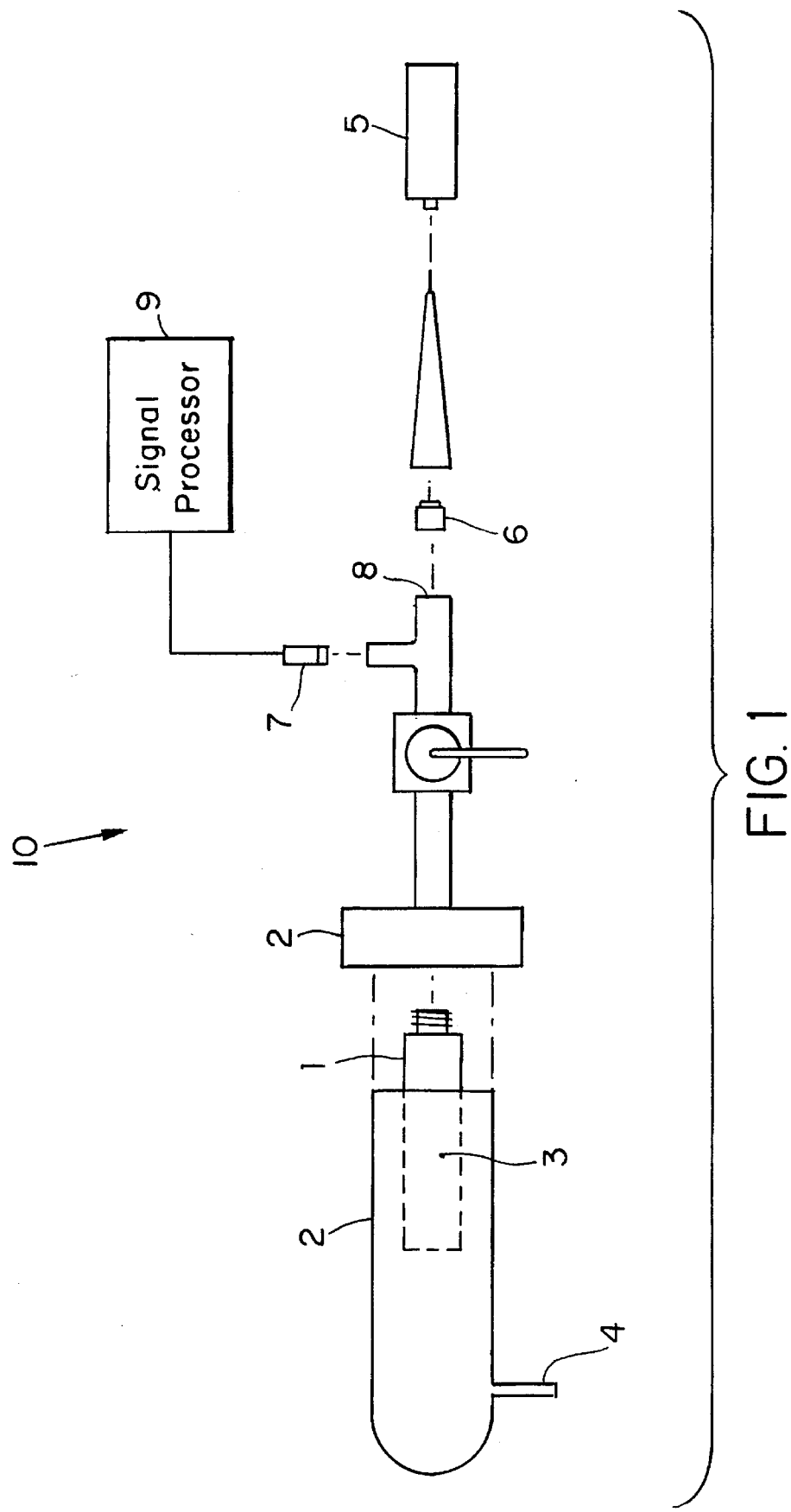
FIG. 1 is a schematic of a preferred embodiment of the current invention with the test housing shown in exploded view.

FIG. 1 shows a system 10 for detecting the presence of a tracer gas for use with, and to thereby determine the integrity and/or pore size characteristics of, porous membrane filter products using the principles of the present invention. Porous membrane filter products include polymeric membrane filters of microfiltration, ultrafiltration and reverse osmosis types, ceramic and metal filters of these classes, as well as related materials used in separation and purification applications. A porous membrane filter product in the form of a pleated membrane cartridge 1, which is to be tested and whose membrane is properly wetted to completely fill the porous structure with water, is placed into a housing 2 (which for sake of clarity is shown in exploded view) such that the entire upstream filter surface 3 is enclosed and isolated from the downstream volume within the central core of the cartridge (not shown). A mixture of carrier gas, such as air, and tracer gas, such as sulfur hexafluoride, is introduced to the housing through port 4 at the desired test pressure, such as 80% of the acceptable bubble-point pressure, as a challenge gas into the upstream side of the housing. The pressurized gas mixture migrates through the wetted membrane, via diffusion and/or convection, and enters into the downstream volume, such as at the central core of the pleated membrane cartridge, as a moisturized gas mixture. The amount of tracer gas contained in the challenge (i.e. the entering pressurized) mixture can vary from 0.2 percent to 100 percent.

A modulated laser light source 5 with wavelength at an absorption line of the tracer gas, such as 10.5514 microns for sulfur hexafluoride, is directed into an open portion 8 of the downstream volume or through an optical window 6 shown in exploded view. Tracer gas present within this downstream volume becomes excited and a resultant pressure wave is generated upon the energy discharge, manifesting itself as an audible sound. A conventional audio microphone 7 (again in exploded view) positioned in the downstream volume detects the pressure wave and creates a corresponding electrical signal. The microphone signal is processed by an electronic processing circuit 9 which develops an output signal suitable for operator warnings and control signals for process controllers, computers, or other electronic or electromechanical devices or equipment and the like.

Other possible modifications to the system 10 include adding a mixer for mixing the gases contained within the downstream volume so that a homogeneous mixture is presented to the illuminating laser beam independent of the actual location of a large pore through which bulk flow will occur. In addition, it should be noted that the term "light source" is intended to encompass all electromagnetic emissions capable of producing a photo-acoustic effect and is specifically not limited to visible light sources.

In operation, the total applied pressure on the upper surface of the membrane of the filter product is set at one level, such as 80% of the acceptable bubble-point pressure of the membrane, in applications intended for determining membrane or device integrity. For applications in which pore size distributions are desired, the total applied pressure will be increased from a low value, such as 3 psig, up to the bubble point of the membrane, which can be as high as 100 psig. The mixture of carrier gas and tracer gas used to challenge the membrane is generally 30–50% carrier and 50–70% tracer gas by volume. This content of tracer gas can be altered to meet the sensitivity requirements of the application, whereby for less critical applications a lower tracer gas content can be used. In addition, the tracer gas can be added at a concentration that varies in time, rather than at a constant level throughout the test.

The modulated light source 5 is a carbon dioxide laser and can be used to scan some fraction of, or the total downstream volume at about 3910 Hz. In the case of a pleated membrane cartridge being tested, the laser can scan the open end of the central core. The electronic processing circuit 9 is simply a bypass filter that will reject all frequencies other than 2×3910 Hz, or 7820 Hz. This is because when the frontal area is scanned, the laser hits the gas molecules twice. Alternatively, the laser can be chopped rather than scanned, and in this instance a 7 watt laser chopped at 7820 Hz will produce an equivalent output signal. Other possible arrangements for signal detection include the use of a synchronous demodulator which is run synchronously with the modulated laser or a lock-in amplifier can be employed.

In a tracer gas mixture which has become moisturized, both the tracer gas and the moisture (e.g. water or water vapor) emit photo-acoustic signals when excited by a light source at a single, fixed wavelength. For integrity test and pore size distribution measurements, the concentration of tracer gas is quite low during the onset time in which the tracer gas is first measured. During the onset time period, the concentration of the moisture component in the moisturized tracer gas mixture can be as large as the signal attributed to the tracer gas. In order to discriminate between the component of interest (tracer gas) and the undesired, interfering moisture signal, the light source 5 is modulated as discussed in the paragraph above at a frequency which preferentially generates an acoustic emission corresponding to the tracer gas while suppressing the emission corresponding to the moisture.

Figure 2:
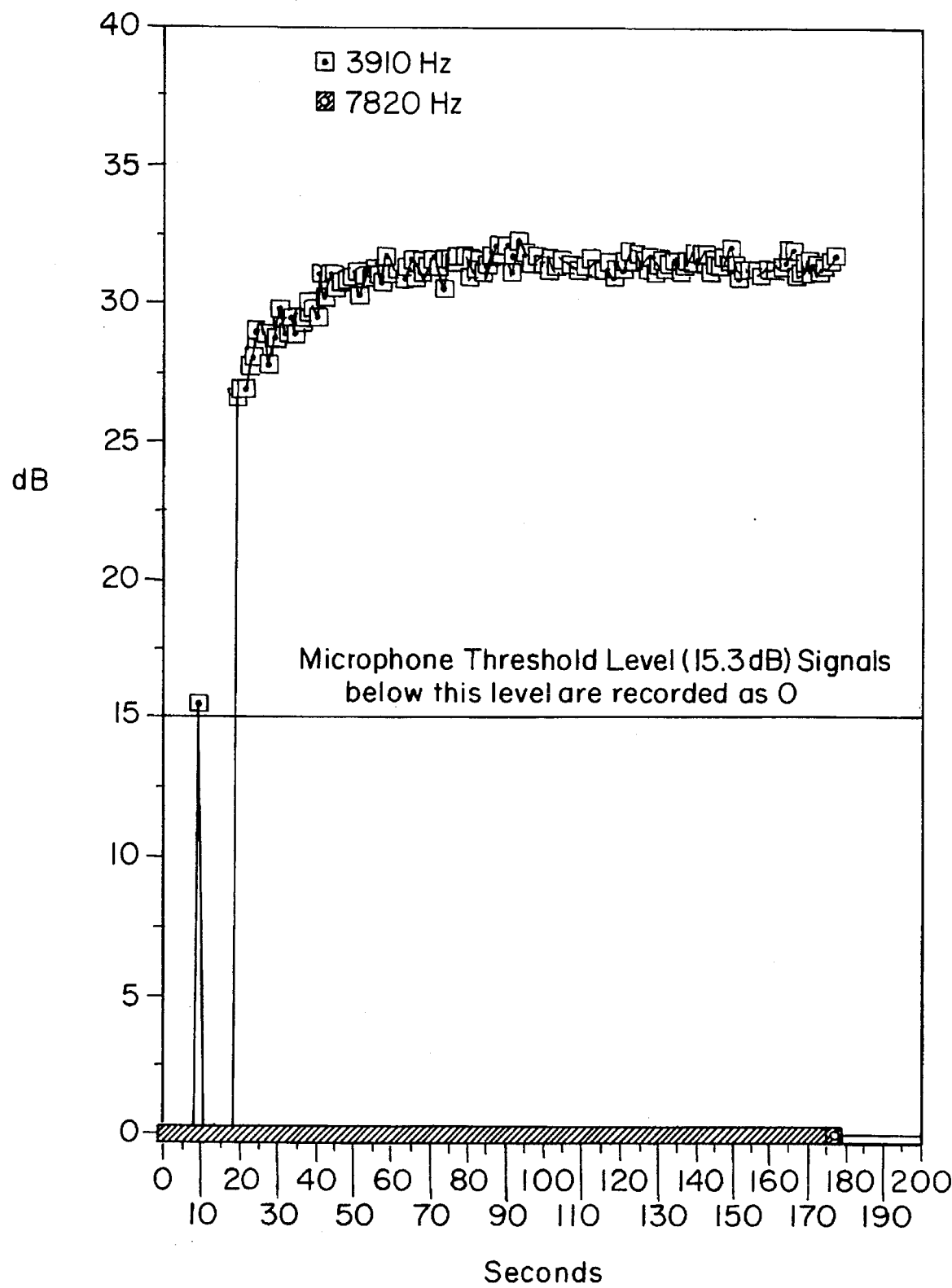
FIG. 2 is a graph showing the effect of modulating the frequency of the incident light beam in suppressing the photo-acoustic signal of an interfering component which absorbs light energy at the same wavelength as that of the component of interest.

An illustration of the above frequency modulation phenomenon is best described by referring to FIG. 2 which shows the results of challenging a water-wet membrane cartridge filter with just an air-carrier gas (no tracer gas). At a scanning frequency of 3910 Hz, a strong signal ($\approx$27 dB) is detected almost immediately after injection of the carrier gas (i.e. at 18 seconds). This signal is attributed to the carrier gas picking up moisture after it exits the downstream surface of the liquid-filled membrane. Under the same test conditions and using the same wavelength of light, but changing the scanning frequency to 7820 Hz, the signal attributed to the moisture drops below the threshold detection level of the microphone 7 (i.e. 15.3 dB) as the moisture does not absorb enough energy during the time period in which the light beam impinges on the water molecules. This is shown in FIG. 2 as a zero-level signal. Note the spike appearing at about 10 seconds in this latter test is an artifact attributed to signal noise at the microphone threshold and does not signify the detection of a signal due to water or water vapor.

Hence, as demonstrated by the foregoing experimental evidence, altering the frequency of the incident light beam reduces the signal from the moisture in the air-carrier gas to a negligible level. Therefore, when $SF_6$ tracer gas is employed under the conditions described above, all signals greater than 15.3 dB will be attributed to the concentration of $SF_6$. While the frequencies presented above are specific for a moisturized mixture of $SF_6$, those skilled in the art using the principles set forth above will be able to determine desired frequencies when other tracer gases, such as carbon monoxide (CO) and carbon dioxide ($CO_2$), are used in place of $SF_6$ without undue experimentation.

The signal generated by an integral membrane unit is characterized by an onset time and a gradual rise over time until the challenge concentration of tracer gas is asymptotically reached. This onset time corresponds to the length of time required for the tracer gas to diffuse across the wetted membrane and build up in the downstream volume until a detectable signal is generated. An onset time of 35–45 seconds has been measured in tests of 7 ft$^2$ pleated cartridge elements. At times greater than this onset time, the concentration of tracer gas will monotonically increase as more tracer gas is diffused into the downstream volume. A non-integral membrane unit is defined as one in which a pore or defect exists whose size is significantly larger than the rated pore size of the membrane. These defects have bubble-point pressures that are lower than the test pressure. Consequently, at the test pressure these defects are evacuated of liquid, and bulk flow, or convection, of both carrier and tracer gas occurs. The onset time for these filters is, therefore, shorter than that of the integral unit, and times of 5–15 seconds for a defective cartridge unit have been observed. Since the tracer gas is migrating to the downstream volume by convection, the rate of increase of its concentration within the downstream volume also occurs much faster than that observed for the integral unit. It is generally understood that, as the size of the defective area is reduced, the onset time will increase until it equals that of an integral unit when the defect area is zero. Correspondingly, the rate of increase in downstream signal will also diminish as the defect area is reduced until it also reaches that of an integral unit when the defect area is zero. These characteristics of these two responses will differ somewhat from the aforementioned behavior if the downstream volume is not homogeneously mixed.

EXAMPLES

Using the general test setup illustrated in FIG. 1, integral and non-integral Durapore® membrane filter cartridges commercially available from Millipore Corporation were inserted into a stainless steel test housing. Sulfur hexafluoride gas was applied under pressure through the port 4. A scanned laser source was used to send a laser field through the acoustically isolated optical window 6 to excite the gas. The acoustic signals generated by excited gas were received by a conventional audio microphone such as commercially available from Tandy Corporation and processed into useful signals in the signal processing circuit 9.

All tests were executed at normal room temperature (approximately 22° C.) and atmospheric pressure on the downstream side of the cartridge. Tests used a mixture of 14.7 psia air and 30.0 psia sulfur hexafluoride applied at 30 psig trans-membrane pressure. Data were collected for each cartridge over a three minute duration. All cartridges were manually water wet, and the cartridge core was drained prior to assembly into the housing. No pre-mixing of the two gases was done. Pure sulfur hexafluoride was introduced into the air-filled (to 14.7 psia) housing until the test pressure was attained. Similarly, the interior of the downstream core was not mixed to achieve homogeneity in these tests.

The results of the tests are shown in FIGS. 3–6 and are further described as set forth below.

EXAMPLE 1

Figure 3:
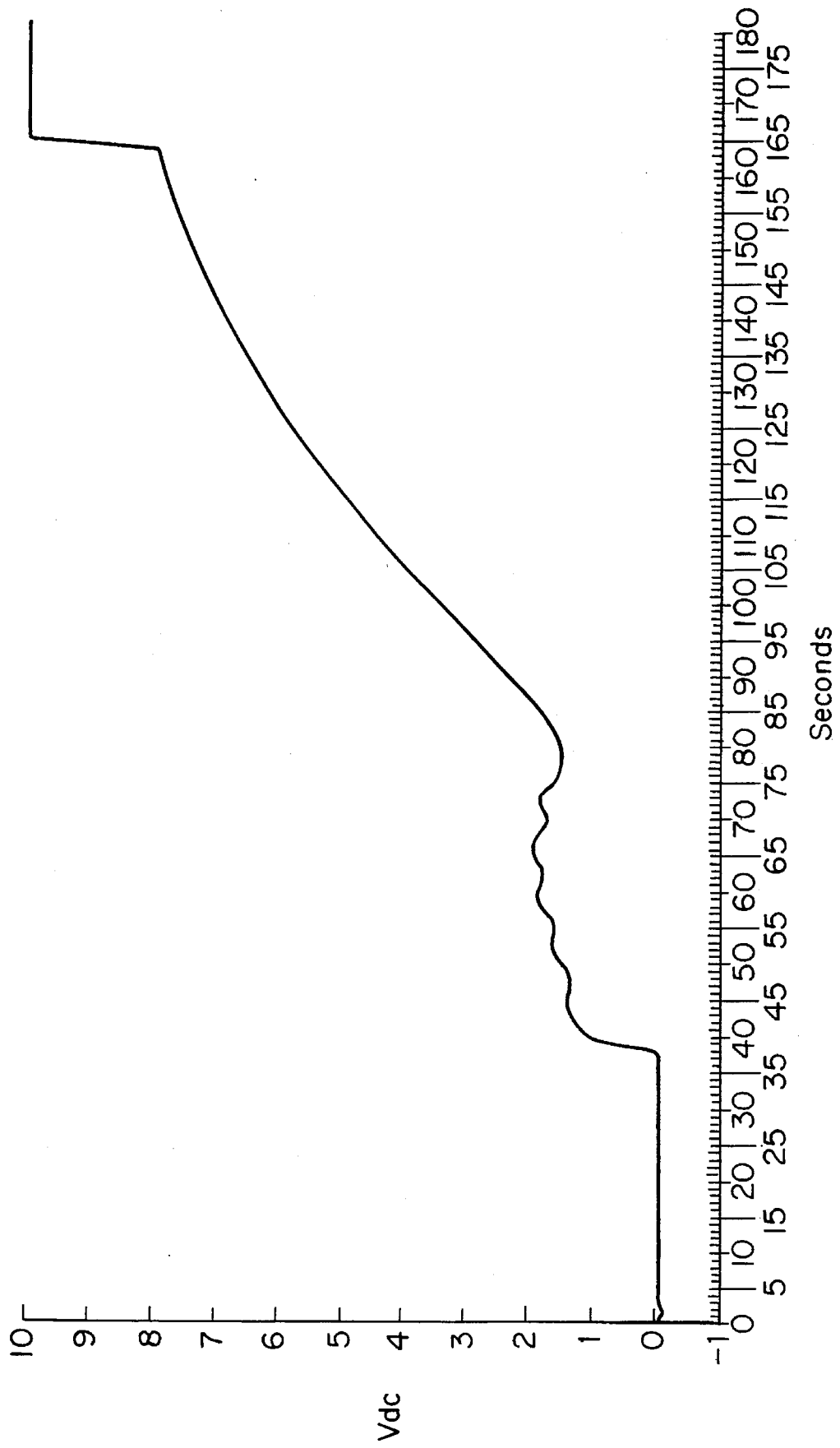
FIG. 3 is a graph showing the response curve of an integral cartridge filter product when challenged with 30 psig of an air-sulfur hexafluoride mixture in accordance with the preferred method of the current invention.

FIG. 3 illustrates a typical response curve associated with a fully integral and bacterially retentive (i.e., zero bacterial counts in the permeate during the standard bacterial challenge test defined in Health Industry Manufacturers Association (HIMA) document No. 3, Vol. 4, April 1982, entitled "Microbiological Evaluation of Filters For Sterilizing Liquids", hereinafter the "HIMA test") Durapore® cartridge device under the aforementioned test conditions. As can be seen, an onset time of about 40 seconds was observed. An initial sharp rise was observed which plateaus at approximately 1.5 vdc (detector circuit output). This plateau was unexpected and may be related to inadequate mixing in the central core. After 75–80 seconds, the response increased smoothly and constantly until the end of the test time.

EXAMPLE 2

Figure 4:
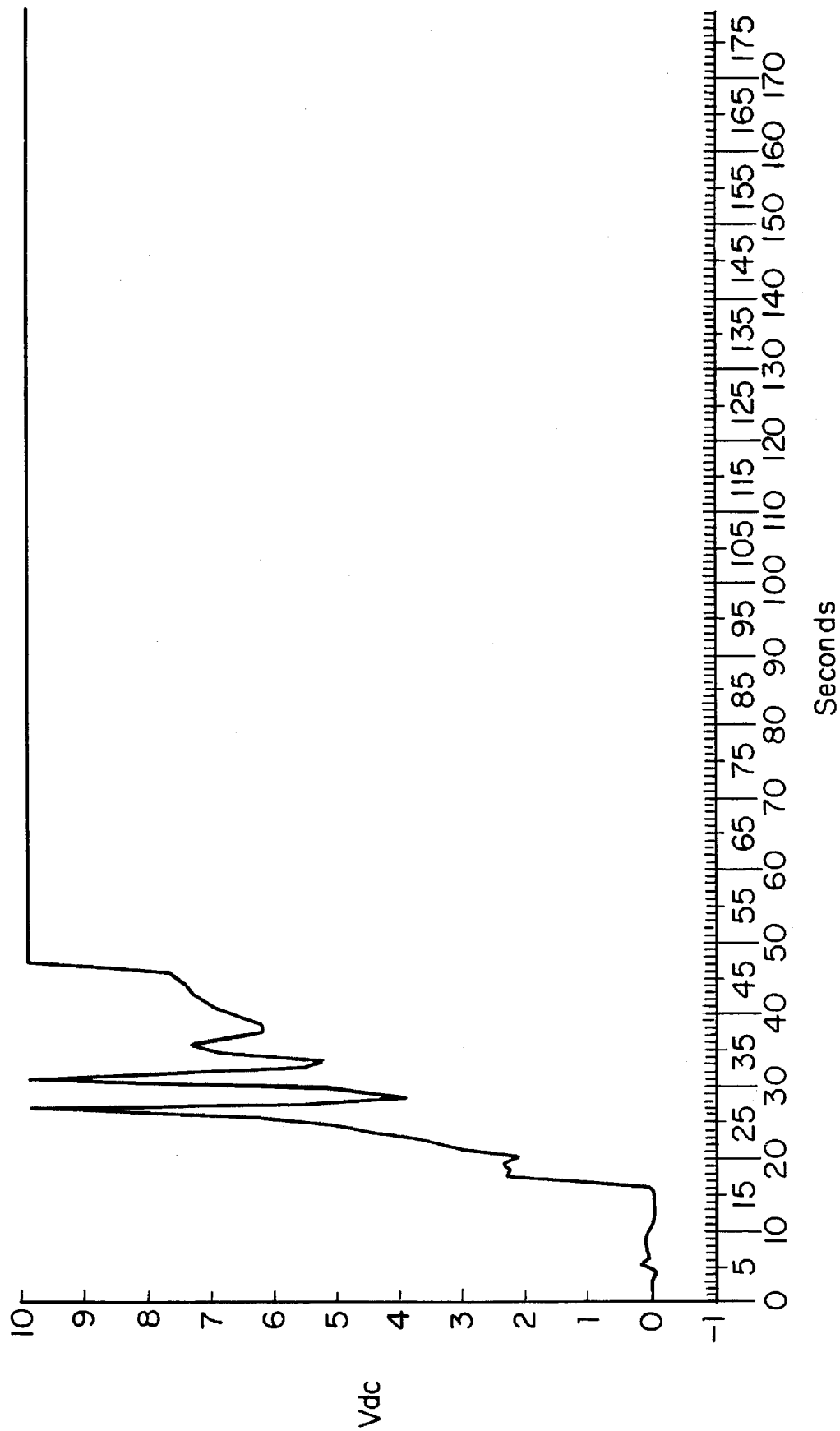
FIG. 4 is a graph showing the response curve of an non-integral cartridge filter product when challenged with 30 psig of an air-sulfur hexafluoride mixture in accordance with the preferred method of the current invention.

FIG. 4 illustrates a response curve representative of a specially manufactured non-integral, bacterially non-retentive (excessively high, >300, bacterial counts in the permeate during the HIMA test), Durapore® cartridge device under the above test conditions. The onset time was observed to be about 16 seconds, significantly less than characteristic of an integral unit as typified in FIG. 3. In addition, the rate of change of the output signal was very steep, exceeding the output voltage capability of the detection circuitry in less than 50 seconds.

EXAMPLE 3

Figure 5:
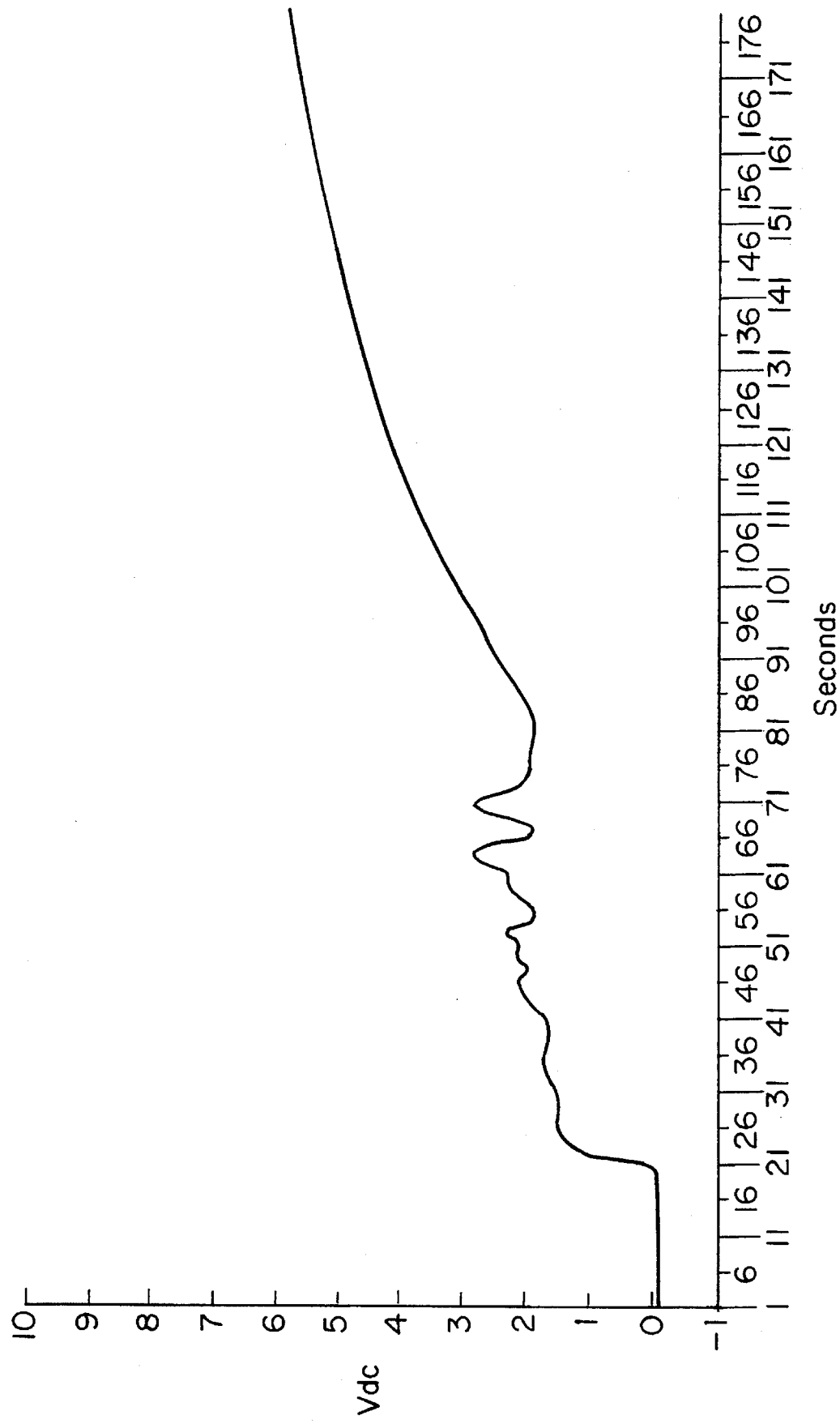
FIG. 5 is a graph showing the response curve of a specially made cartridge that achieves only a >5 log *Pseudomonas diminuta* retention instead of the typical >7 log retention of an integral filter when challenged with 30 psig of an air-sulfur hexafluoride mixture in accordance with the preferred method of the current invention.

FIG. 5 illustrates the behavior of a cartridge specially made to allow very small amounts of bacterial passage (plaque counts of 10–100 in the HIMA test). As can be seen, the onset time is about 21 seconds, which is in between the fully retentive (40 seconds) and the fully non-retentive (16 seconds) cartridges shown in FIGS. 3 and 4. The rate of rise of $SF_6$ concentration in this experiment was slow and prolonged when compared with that of the integral cartridge. This result is most likely the result of mixing effects in the downstream cartridge core. However, as witnessed by the onset time differences, this defective cartridge, while being difficult to identify with the HIMA test, is easily distinguished from the integral unit in accordance with the methods of the present invention.

EXAMPLE 4

Figure 6:
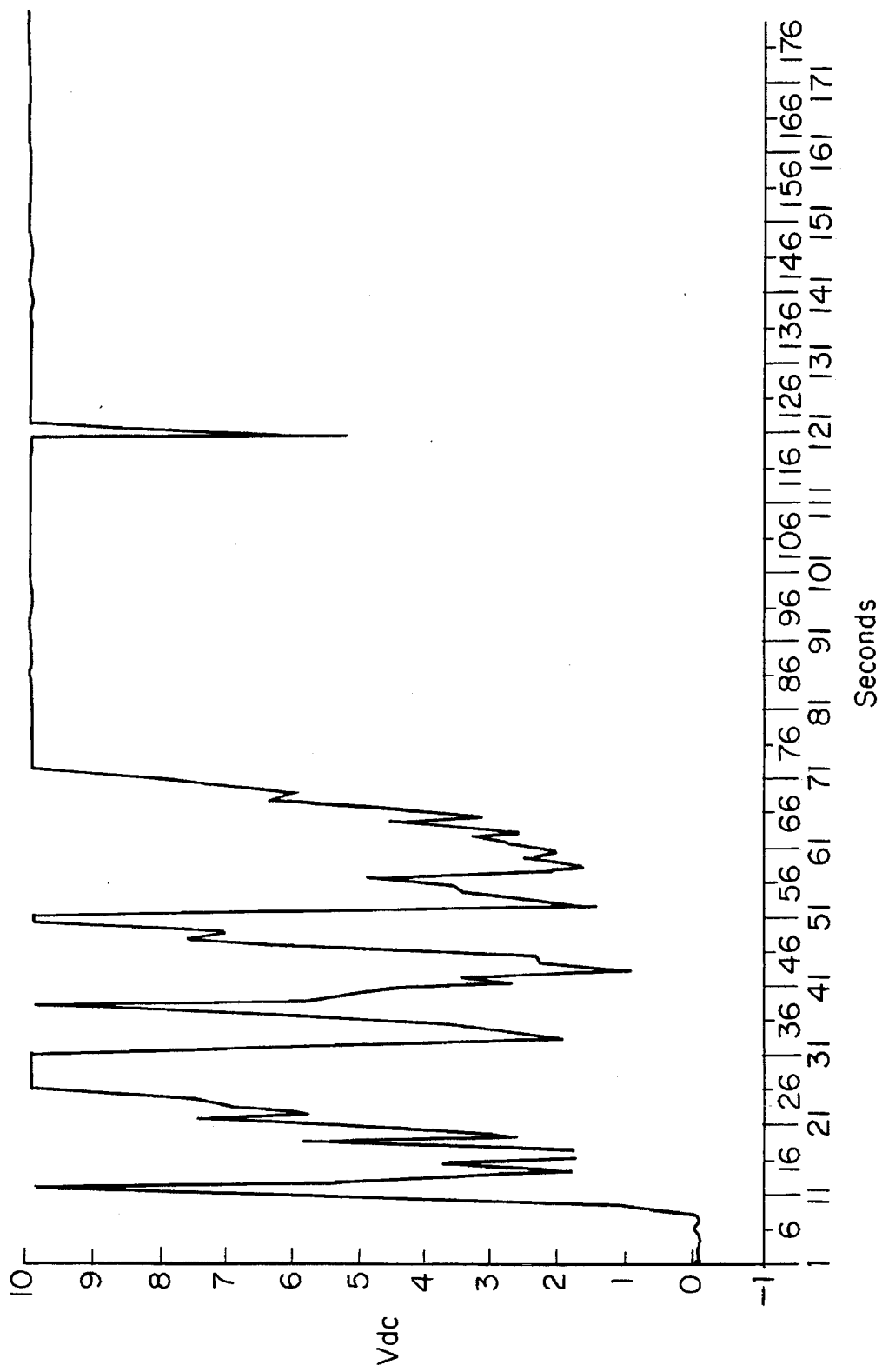
FIG. 6 is a graph showing the response curve of an integral cartridge filter product with a controlled-size 3 micron diameter hole artificially introduced when challenged with 30 psig of an air-sulfur hexafluoride mixture in accordance with the preferred method of the current invention.

FIG. 6 illustrates a response curve of an integral and bacterially retentive Durapore® cartridge within which was created with a single 3.0 µm hole. As can be seen, the onset time was very rapid, occurring at about 8 seconds. The response curve increased nearly instantaneously to a rate exceeding the detector output capability. The response after this rapid rise was erratic, spiking and decreasing several times until the detector output was permanently exceeded at about 75 seconds. This erratic behavior is again most likely due to mixing phenomena. However, this example clearly demonstrates that the procedure of the present invention is useful to easily distinguish the presence of a single defect of 3 µm diameter from an integral unit. In addition, this result suggests that this test system is not only rapid, but also has the capability for extreme sensitivity, While the invention has been explained with respect to a preferred embodiment thereof, it is contemplated that various changes may be made in the invention without departing from the spirit and scope thereof. Changes and modifications of the specifically described embodiments can be carried out without departing from the scope of the invention and is intended to be limited only by the scope of the appended claims.

I claim:

1. A process for determining the integrity and/or pore size characteristic of a porous membrane structure alone or in a fabricated device comprising:

wetting said membrane structure with a liquid to fill the pores of the membrane structure;

placing said liquid-filled membrane structure in an ambient air environment;

introducing a challenge gas mixture in proximity to a first surface of said membrane structure, said mixture being applied under pressure to said first surface to cause said gas mixture to migrate through the pores of said membrane structure and to exit from a second surface thereof as a moisturized gas mixture into said ambient air environment;

exciting within said ambient air environment said moisturized gas mixture after it exits said second surface with a light beam having a wavelength that is absorbed by one or more components of said moisturized gas mixture;

modulating said light beam at a frequency so that a component of interest within said one or more components of said moisturized gas mixture preferentially generates an acoustic emission;

detecting said acoustic emission; and generating an electrical signal proportional to said acoustic emission.

2. The process of claim 1 wherein one component of said challenge gas mixture varies while said challenge gas mixture is being introduced in concentration from 0.2 percent to 100 percent.

3. The process of claim 2 wherein said one component is sulfur hexafluoride gas.

4. The process of claim 2 wherein said one component is carbon dioxide.

5. The process of claim 1 wherein said challenge gas mixture comprises air and sulfur hexafluoride gas.

6. The process of claim 1 is wherein the differential trans-membrane pressure under which said challenge gas mixture is applied is varied from 3 psig to the bubble point of said membrane.

7. The process of claim 1 wherein said modulating step is accomplished by scanning said light beam across at least a portion of the volume downstream of said membrane structure.

8. The process of claim 1 wherein said modulating step is accomplished by chopping said light beam.

9. The process of claim 1 wherein said challenge gas mixture is premixed prior to being applied under pressure to said one surface.

10. The process of claim 1 wherein said challenge gas mixture includes a carrier gas applied under pressure to said one surface and a tracer gas to be detected which is injected and mixed with said carrier gas after application of said carrier gas.

11. The process of claim 10 wherein said gas to be detected is sulfur hexafluoride.

12. The process of claim 11 wherein said one component is sulfur hexafluoride gas.

13. The process of claim 1 wherein said one component of said gas mixture is soluble in said liquid.

14. The process of claim 1 wherein a laser is used to excite said one component of said gas mixture.

15. The process of claim 14 wherein the laser is modulated synchronously.

16. The process of claim 1 wherein a laser is used to excite said one component of said gas mixture, said laser being scanned across at least a portion of the volume downstream of said second surface of said membrane structure.

17. The process of claim 1 wherein a laser is used to excite said one component of said gas mixture, said laser being fixedly positioned behind said second surface of said membrane structure and the beam of said laser being alternatively passed and then blocked to provide a chopped beam impingement on the volume downstream of said second surface.

18. The process of claim 1 wherein said electrical signal represents a measure of the time from which said one component is introduced to said one surface to the detection thereof after said one component exits said second surface.

19. The process of claim 1 wherein said electrical signal represents a measure of the rate of change of the concentration of said one component detected after said one component exits said second surface.

20. The process of claim 1 wherein said gas mixture within the volume downstream of said second surface is mixed to present a homogeneous mixture to said light beam.

21. The process of claim 1 wherein said light beam is monochromatic.

22. A process for determining the integrity and/or pore size characteristic of a porous membrane structure alone or in a fabricated device comprising:

wetting said membrane structure with a liquid to fill the pores of the membrane structure;

introducing a gas mixture in proximity to a first surface of said membrane structure, said mixture being applied under pressure to said first surface to cause said gas mixture to migrate through the pores of said membrane structure and to exit from a second surface thereof;

mixing said gas mixture within the volume downstream of said second surface to produce a homogeneous gas mixture;

exciting said homogeneous gas mixture with a light beam at a wavelength that is preferentially absorbed by a component of interest within said mixture to generate an acoustic emission;

detecting said acoustic emission; and generating an electrical signal proportional to said acoustic emission.

* * * * *